United States Patent [19]

Elliott

[11] Patent Number: 5,022,045
[45] Date of Patent: Jun. 4, 1991

[54] OPTICAL-TYPE, PHASE TRANSITION HUMIDITY-RESPONSIVE DEVICES

[76] Inventor: Stanley B. Elliott, 7125 Conelly Blvd., Walton Hills, Ohio 44146

[21] Appl. No.: 547,314

[22] Filed: Jul. 5, 1990

Related U.S. Application Data

[63] Continuation of Ser. No. 312,601, Feb. 17, 1989, abandoned, which is a continuation of Ser. No. 194,345, May 16, 1988, abandoned, which is a continuation of Ser. No. 763,003, Aug. 6, 1985, abandoned.

[51] Int. Cl.$^5$ ............................................. G01N 25/12
[52] U.S. Cl. ........................................ 374/20; 374/17; 374/18; 73/336.5
[58] Field of Search ...................... 374/16, 17, 18, 19, 374/20, 45, 1; 73/73, 336.5, 336, 335; 252/962, 963

[56] References Cited

U.S. PATENT DOCUMENTS

| | | | |
|---|---|---|---|
| 1,933,803 | 11/1933 | Hickman | 73/336.5 |
| 2,554,440 | 5/1951 | Coburn | 73/336.5 |
| 2,877,683 | 3/1959 | Fischer | 374/45 |
| 3,166,928 | 1/1965 | Jackson | 374/20 |
| 3,350,789 | 11/1967 | Davies | 73/73 |
| 3,607,782 | 9/1971 | Rosen | 73/73 |
| 3,776,038 | 12/1973 | Elliott | 73/335 |
| 3,810,389 | 5/1974 | Jason | 73/336.5 |
| 3,863,503 | 2/1975 | Elliott | 73/336 |
| 4,083,249 | 4/1978 | Gerber | 73/336.5 |
| 4,166,891 | 9/1979 | Elliott | 252/192 |
| 4,345,455 | 8/1982 | Hayes | 374/20 |
| 4,612,802 | 9/1986 | Clarke et al. | 73/73 |

Primary Examiner—Thomas B. Will
Attorney, Agent, or Firm—Baldwin, Egan & Fetzer

[57] ABSTRACT

The invention is directed to chemical compositions suitable for use in salt-solution transition temperature or hot mirror devices. It also provides methods of using these sensors (for the measurement of the humidity of gases) as well as the apparatus. The chemical composition which of itself senses the changes of water vapor pressure is birefringent at a first water vapor pressure and temperature, but non-birefringent at a second vapor pressure and temperature. The optical changes which accompany these phase changes may be amplified with polarizers. The means for heating the chemical composition can vary widely. Various thermometric devices can be used for temperature sensing. The accuracy required of the particular instrument model, the device's configuration, and the other components, selected for the particular system all affect the choice of thermometric device selected. The light detector is responsive to observable changes in the brightness and intensity of the light emerging from the chemical composition, the light from the composition at a particular water vapor pressure and temperature being of sufficient brightness and intensity to provide an optical signal to activate the light-detecting electrical means.

21 Claims, 7 Drawing Sheets

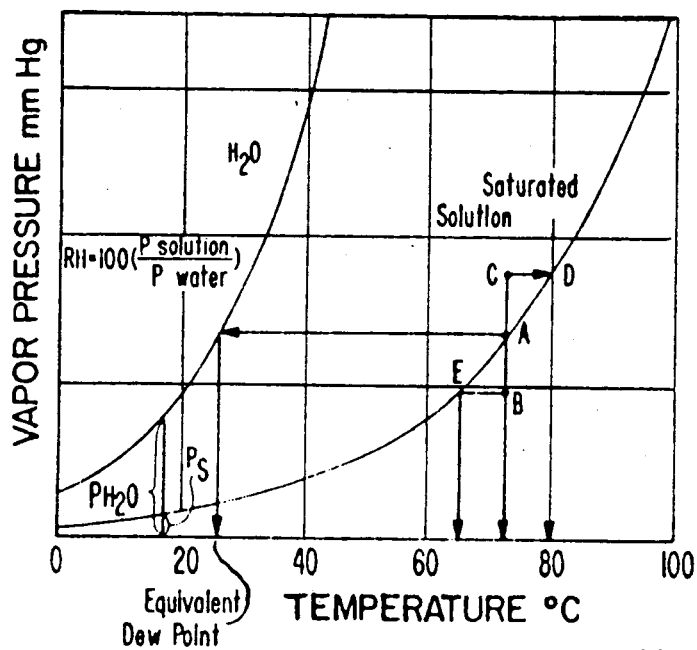
Fig. 5
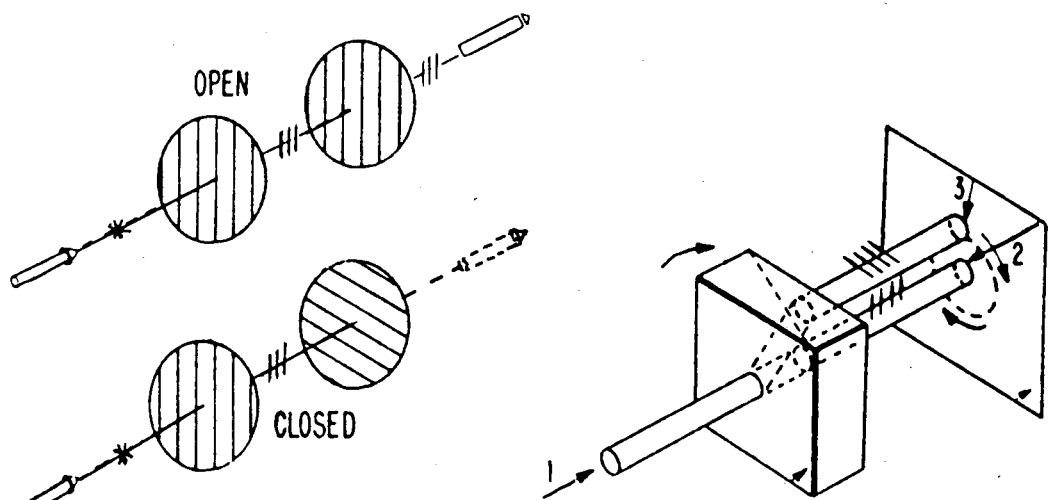
Fig. 6
Fig. 7

Linear Polarizer Layer + Quarter Wave Layer = Circular Polarizer

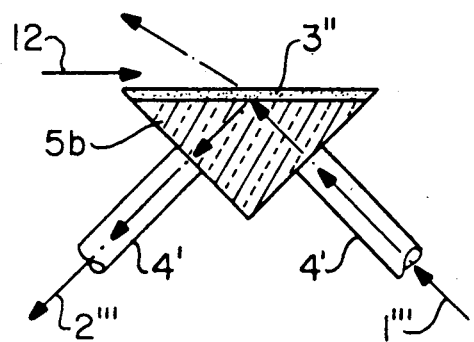
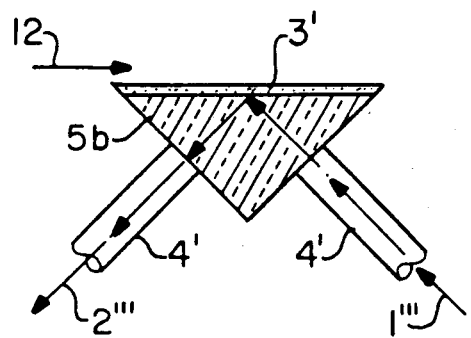
Fig. 14A Fig. 14B
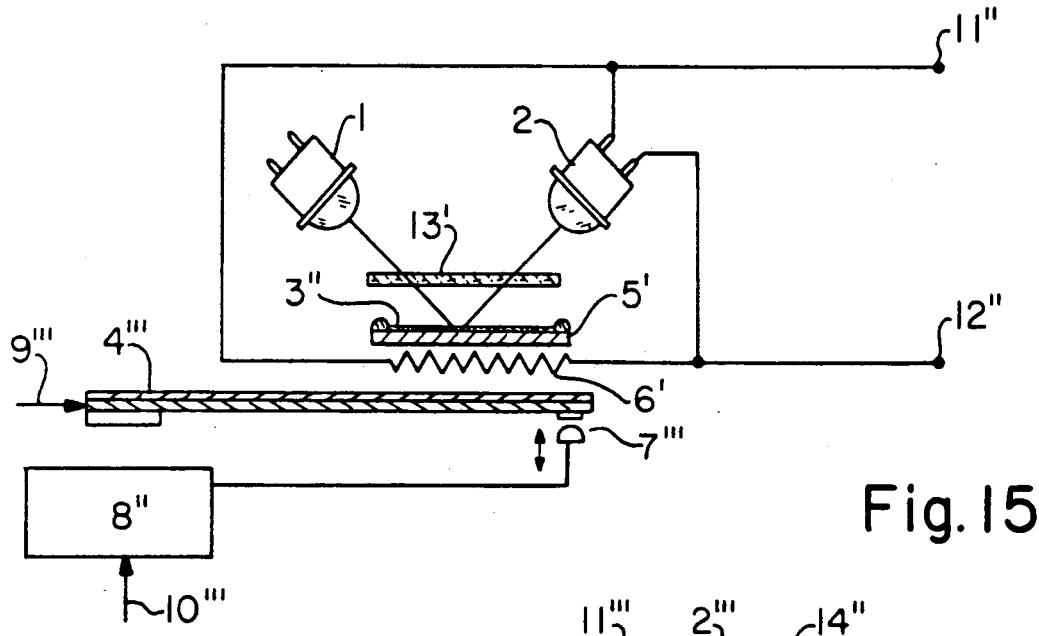
Fig. 15
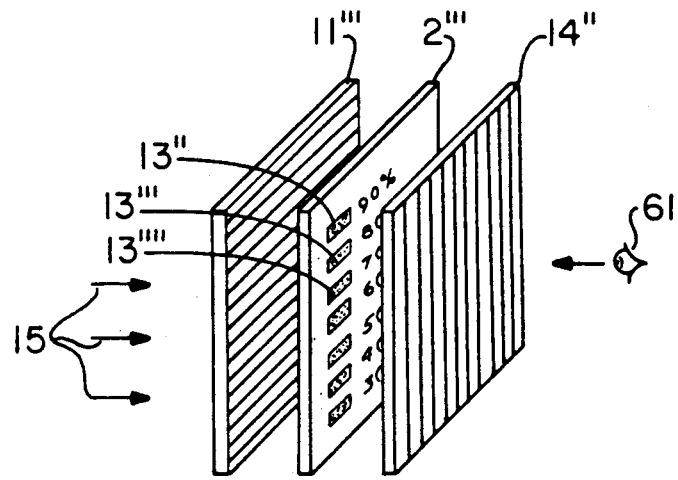
Fig. 16

Optical Readouts
(Polarizer Amplification)
Fig. 17A Solid/Solid Phase Shift
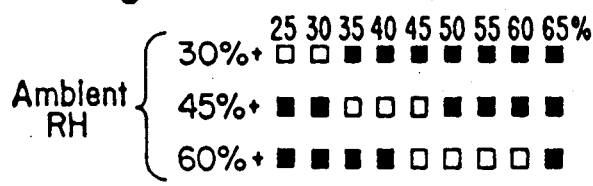
Hygrometer Scale Appearance
Read highest bright □
Square
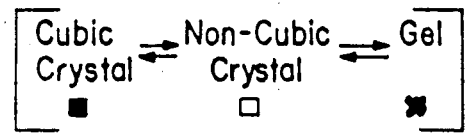
Fig. 17B Solid/Gel Phase Shift
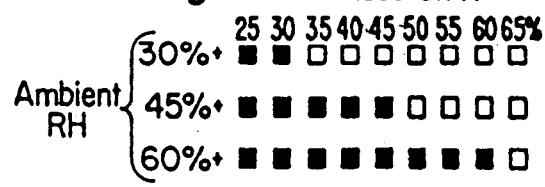
Hygrometer Scale Appearance
Read highest bright ■
Square
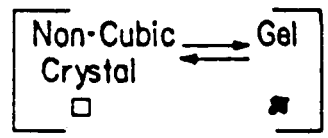
Full Readout of Solid/Solid Sensors
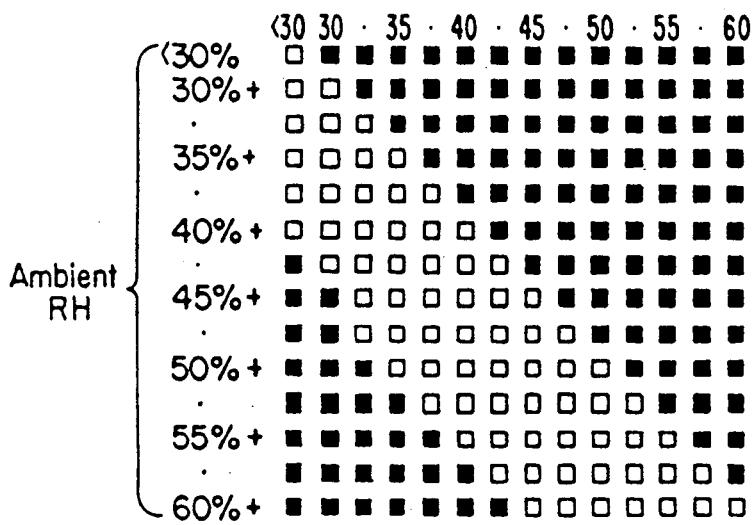

OPTICAL-TYPE, PHASE TRANSITION HUMIDITY-RESPONSIVE DEVICES

This application is a continuation of application Ser. No. 312,601 filed Feb. 17, 1989, now abandoned, which is a continuation of Ser. No. 194,345, May 16, 1988, abandoned, which is a continuation of Ser. No. 763,003, Aug. 6, 1985, abandoned.

BACKGROUND OF THE INVENTION

In response to the world wide need of modern societies for the indication and control of the humidity of myriad processes and locations in commerce, industry, the sciences, and the consumer world, scores of hygrometric devices have been developed. Nearly all of these have been "secondary" devices which depend on non-reproducible processes (such as moisture sorption by various materials) and as a result the devices have no inherent accuracy, drift badly with time, and are only suitable for undemanding needs.

Only a very few inherently accurate "primary" electronic devices based on unvarying physical phenomena have been developed. These have been characterized by very high cost, high power consumption, and large sensor bulk and equipment size. Thus, myriad applications are being served inadequately at present. Heading the very short list of primary electronic instruments is the "dew temperature" or "cold mirror" hygrometer, shown in its modern, thermoelectrically cooled version in FIG. 1. Its flexibility of application, ease of use, and accuracy make it the primary instrument of choice for the majority of demanding applications where its high cost, bulk, and power needs can somehow be tolerated. A primary device free of these limitations has been badly needed. Such a device would permit significant improvements in control and product quality in many applications of importance.

A study of my U.S. Pat. Nos. 3,776,038, 3,863,502, 4,166,891, and 4,175,207 suggests that a new type of primary hygrometer might be possible, based on the teachings of these patents. It would be analogous to the cold mirror hygrometer of FIG. 1. However, instead of securing an optical signal from dew formation at a particular temperature on a cooled mirror, the optical signal would come from the phase shift at a particular temperature of a single suitable salt on a heated mirror. The phase shift could be solid/solid (an isotropic crystal changing to an anisotropic crystal) or solid/liquid (an anisotropic solid changing to an isotropic solution). There is a wider choice of sensing salts which undergo the solid/liquid phase shift than of those which undergo the solid/solid change. Thus, the solid/liquid change would be the sensing mode of greatest interest. However, the same concepts would apply to the solid/solid mode of sensing.

If the art taught in the patents mentioned were used, and especially if polarized light were used for signal amplification, a suitable humidity sensing system would then include these basics: (1) a source of illumination which provides a light beam, (2) means for providing observable changes in humidity comprising a chemical composition which of itself can sense changes in humidity, the chemical composition (through a change in the degree of hydration) being abruptly triggered to an isotropic/ anisotropic phase change at a particular water vapor pressure/temperature, (3) means for heating said composition to the phase change temperature of the particular chemical composition for that water vapor pressure, (4) means for determining the temperature of the chemical composition at the phase equilibrium point, (5) light detecting means for detecting a pre-selected brightness of light emerging from the film at the equilibrium point and so providing a signal, and (6) an empirically established graph of water vapor pressure vs temperature defining the particular chemical composition's equilibrium curve for the phases sensed. From this curve the dew temperature equivalent of any temperature on the equilibrium curve can be readily determined.

Such a device would have the same useful characteristic as dew temperature hygrometers, namely, giving a continuous readout of humidity, e.g. from 5.0% RH to 100% RH, from a single salt. By way of comparison, the direct readout hygrometers now being made commercially under these patents also offer high utility and stability, and freedom from drift. However, they give discrete readouts of humidity, e.g. 30.0% RH, 32.5% RH, 35.0% RH, 37.5% RH, etc. A continuous readout is often essential and the type just proposed would be free of many of the limitations which characterize the standard dew point hygrometer.

Originally, as explained above, it appeared that by utilizing the unvarying physical phenomena centering on the hydration of a single "optically-responsive" salt the essential requirements could be met. A very small mass of a selected material could be illuminated and scanned by one of the widely available, exceptionally compact, "light source/ light responsive" pairs of optoelectronic devices to generate large electrical signals which could readily be used in indicating and controlling functions.

Unfortunately, the wide circulation of information regarding the availability of these patents for license (along with suggestions for the design and fabrication of what was termed a "saturated salt-type dew point" device) brought no successful development by any of a number of corporations which manufacture or use hygrometric devices. The reason was that the device which was so interesting theoretically could not be made to work in practice. Chemical compositions simply did not perform in the analogous device the way water (as dew) functions in the classic dew point hygrometer.

Subsequently, my extensive research and development has now established that what is required of a chemical composition (for it to perform through heating what water performs through cooling in a dew point device) includes the following novel features:

1) Long Term Stability

The sensing substance, water (as dew), is continually refurbished from the air in standard dew temperature devices. Thus, stability is of no concern. By way of comparison, the chemical composition of the proposed "saturated salt" device or, more accurately, "salt-solution transition temperature" device must be chemically and physically stable for long periods at high temperature in the presence of dust, etc. Such a device hereafter will be termed a "hot mirror" device, analogous to standard cold mirror devices.

2) Low Tendency to Supersaturate

Though liquid water as dew can be slightly supercooled before forming ice, a large number of salts of apparent use as humidity sensors are found in practice to supersaturate severely and with great ease. By "supersaturate" is meant to form solutions in which the solute is more highly concentrated than equilibrium curves would seem to permit. To function satisfactorily as a humidity sensor, the composition's tendency to supersaturate must be minimal or absent if serious error is to be prevented.

3) High Degree of Birefringence

The optical signals generated emanate from birefringent crystals. In order to have adequate sensitivity to changing humidity, the sensing layer of liquid and solid must be very thin. Thus, very small amounts of birefringent crystals must pass considerable amounts of light. This requires that the birefringence of the composition be very great, a phenomenon seldom encountered in nature.

4) High Melting Point

Hydratable inorganic compounds usually have high heat stability and high melting points, but few have high birefringence. Organic compounds theoretically have a better chance of exhibiting the essential high birefringence for optical signalling. However, they are ordinarily unstable thermally and/or melt at low temperatures. The humidity-sensing composition obviously cannot melt within the temperature range necessary for effective humidity sensing.

5) Rapid, Reversible Response to Shifting Equilibrium Points

Chemical compositions may react with water vapor at varying rates, depending on the "activation energy" of the particular compound. Most applications for direct readout, discrete sensor hygrometers (such as have been described above) do not require high speed hydration of the sensing compositions. In contrast, the sensing compositions suitable for hot mirror devices must have a high speed of hydration, born of low activation energies. Indeed, hydration must be almost instantaneous if severe "overshooting" and "hunting" of optical/electronic systems based on such sensing compositions is to be avoided.

The sensing composition also must preserve its integrity as a signalling agent at high temperatures by remaining reversible. That is, it cannot shift structure to a new crystal form which has wholly new features such as, for example, different water solubility. Neither can the chemical composition bind the water so tightly that it cannot readily release its water on a slight elevation of temperature.

6) High Water Solubility for Low Humidity Sensing

In order to effectively compete with standard dew temperature hygrometers, the hot mirror device should be capable of sensing rather low humidity levels (low dew point temperatures). This usually requires the use of salts having extremely high water solubilities (and thus low water vapor pressures).

There are exceptionally salts whose solubility is exceptionally high. In the patents mentioned above, the lowest relative humidity (RH) noted to cause a solid/solid transition is that for the rubidium salt of 3,3'4,4' bensophenone tetracarboxylic acid. The transition occurs at 18% RH at room temperature. This pure salt, however, is unusable in the device considered here because the extreme slowness with which it dehydrates makes it virtually an irreversible sensor. The lowest RH noted in the patents for a solid/liquid transition is that for the potassium salt of levulinic acid at 30% at room temperature. Thus, to sense low humidities is inherently very difficult.

To simultaneously meet all of the essential criteria mentioned is exceptionally complex and is what has accounted for the failure to devise workable hot mirror devices. These itemized requirements in several instances refer only to solid/liquid systems, though solid/solid systems are also possible. However, as noted before, there is a more limited choice of potential solid/solid sensors.

SUMMARY OF THE INVENTION

The present invention provides novel chemical compositions suitable for use in "salt-solution transition temperature" devices or, as I term them, "hot mirror" devices. It also provides methods of using these sensors (which are especially suitable for the precise measurement of the humidity of gases) as well as the apparatus.

As a result of intensive and extensive research and development I now have devised suitable sensors, as well as compounding methods to be used with them. Further, I have discovered empirically, after extensive work, that the classic "dew point" or "cold mirror" hygrometer which has evolved over many decades of development is inherently unsuitable for use (in an unmodified form) as a device for practicing hot mirror optical hygrometry using salt films as sensors. That is, the "cold mirror" structure requires important changes in the configuration of key elements of the device (even when potantially excellent sensing salts are used) if acceptable speed of response, accuracy, and freedom from overshoot and/or undershoot are to be secured when it is operated as a "hot mirror" device.

The devices and methods of the new hygrometry allow many variations on the primary requirements. For example, light sources such as LEDs, tungsten lamps, neon lamps, etc. can be used with a variety of light detecting means such as photo-transistors, photo-SCRs, photodiodes, photo-resistor cells, etc.

The chemical composition which of itself senses the changes of water vapor pressure is birefringent, translucent, and anisotropic at a first water vapor pressure and temperature, but non-birefringent, optically clear, and isotropic at a second vapor pressure and temperature. The optical changes which accompany these phase changes may be amplified by passing the light beam through a polarizer and passing the polarized beam through the composition and then through an analyzer to a detector.

The means for heating the chemical composition can vary from simple heating elements of resistance wire to thermistors used in the self-heating mode.

Thermometers, thermistors, platinum resistance thermometers, and other devices can be used for temperature sensing. The accuracy required of the particular instrument model, the device's configuration, and the other components selected for the particular system all affect the choice of thermometric device selected.

The light detector may be the eye or a suitable photodevice. The detectors are responsive to observable changes in the brightness and intensity of the light emerging from the chemical composition, the light from the composition at a particular water vapor pressure and temperature being of sufficient brightness and intensity to provide an optical signal to activate the light-detecting electrical means.

The concept of a multi-sensor, optical-type, humidity-responsive device utilizing compositions which of themselves sense changes in humidity and concurrently undergo useful optical changes was disclosed in my U.S. Pat. No. 3,776,038. Precision, direct readout, visual-type solid/solid phase shift hygrometers are now in large scale, commercial production in the U.S. using this technology, as noted before. Further, the concept of a device responsive to humidity and temperature changes, utilizing an appropriate sensing composition, was disclosed in my U.S. Pat. No. 3,863,502.

The concept of utilizing the salt-solution phase change or transition temperature to indicate a temperature from which the dew point can be derived is not new. However, using optical changes which accompany salt-solution phase changes is novel and it makes possible my new type of meter. For example, commercial "saturation temperature hygrometers" are based on the electrical conductivity changes of a heated lithium chloride sensor exposed to the atmosphere whose humidity is to be sensed. Such sensors must use large masses of sensing salt and so are sluggish in response and of limited accuracy. However, using the optical changes which occur at the phase transition point of special salts allows the use of very thin, low mass films which can exhibit a very high speed of response and which generate data of great accuracy. As explained before, the new type of hot mirror hygrometer is similar in many ways to the modern cold mirror hygrometer shown schematically in FIG. 1. However, instead of an optical signal from dew formation on a cooled mirror, the signal comes from the formation of anisotropic salt crystals in a solution of a single, highly deliquescent salt on a heated mirror. The mirror's evaporation surface is maintained electronically in vapor pressure equilibrium with the gas being sampled. Crystallization is detected by optical techniques using polarized light. When maintained at the temperature at which the rate of evaporation exactly equals the rate of condensation, the evaporation surface is at the "salt-solution transition temperature." Knowing such a temperature allows establishing the standard dew temperature equivalent for the particular salt from its empirically determined equilibrium curve.

There are many advantages which such a meter possesses. It has been mentioned that a small, light weight, low power heating element replaces bulky, complex, expensive, high power thermoelectric coolers, ordinarily used in multiple stages. Thus, very compact, light weight, rapidly responding systems can be assembled which are suitable for radio sondes to be air dropped for meteorological purposes. Until now, so-called "secondary" instruments (based on non-exact, drifting, physical phenomena such as sorption processes) had to be used in order to secure light weight and compactness. The calibrations of such secondary standards drift badly during storage, often making difficult, field restandardization necessary. The new system, being a primary standard, does not drift.

There are still other advantages. Thus, though dew temperature hygrometers are primary instruments, there are inherent errors associated with the vapor pressure of the minute spheres or droplets of water which comprise the "dew" which forms on the mirrors of such instruments. The continuous films of fluid which form on the mirror in practicing the present method are free of this problem and so the results are more accurate. Further, the errors generated when traces of contaminating salts form on standard dew point mirrors (from salt particles in the sampled gas) are much reduced with the present system since the salt sensing film can be regarded as a "pre-contaminated" film.

Still another advantage of the new system lies in the fact that either transmission- or reflection-type systems can be used, whereas dew point hygrometers can utilize only the reflection mode. In some situations where mirror corrosion is a problem, the transmission mode of operation can be highly effective. Instrument design can also be more flexible using the transmission mode, as will be shown later.

THE DRAWINGS

FIG. 5 shows the vapor pressure-temperature curves for water and the hydrate $MA \cdot sH_2O$.

FIG. 6 shows the light transmission through linear polarizers.

FIG. 7 shows the light transmission in a crystal which has two indices of refraction (birefringent).

FIG. 14A is a cross-sectional view of a reflection mode system incorporating the present invention;

FIG. 14B is a view similar to FIG. 14A but with the sensing salt in isotropic solution.

FIG. 15 is an electromechanical type of hygrometric control.

FIG. 16 is a view of a transmission mode, solid/liquid phase shift hygrometer.

FIG. 17A illustrates the three optical shifts shown by solid/solid phase shift sensors as the humidity changes.

FIG. 17B illustrates the two optical shifts shown by solid/liquid phase shift sensors as the humidity changes.

DETAILED DESCRIPTION OF THE INVENTION

Figure 1:
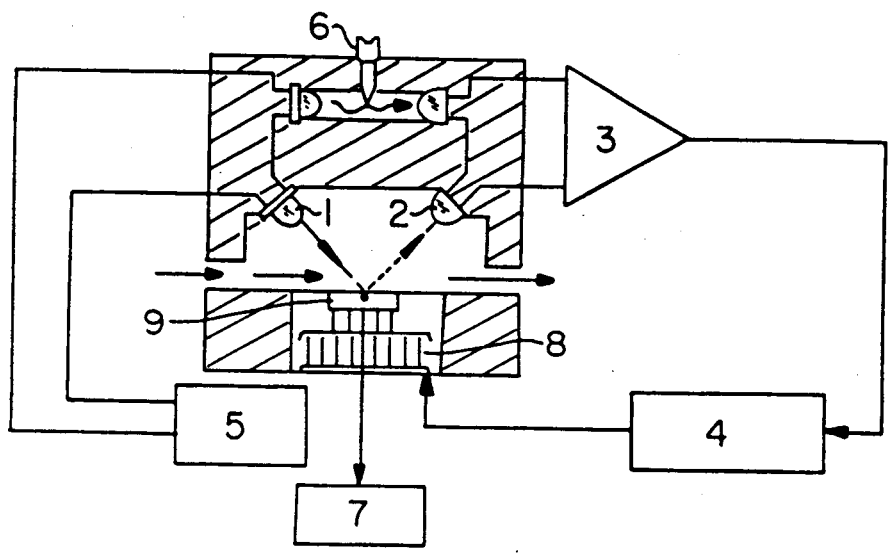
FIG. 1 is a schematic view of a standard prior art "cold mirror" hygrometer.
Figure 2:
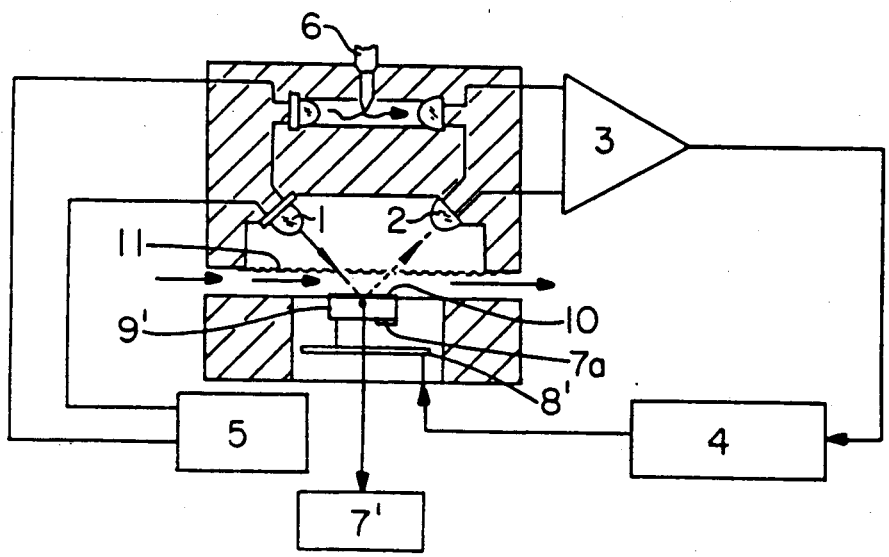
FIG. 2 is a schematic view of a "salt-solution transition temperature" or "hot mirror" hygrometer using the "reflection mode" of operation.

As noted before, FIG. 1 is a schematic view of a standard "cold mirror" hygrometer. FIG. 2 is a representative embodiment of a "hot mirror" hygrometer. They contain elements which have interesting parallel functions. In each of these figures LED 1 projects a light beam onto mirror 9 from which it is reflected, if conditions are appropriate, to light detector 2. In the case of FIG. 1 the amplifier 3 controls the power of the thermoelectric cooler power supply 4 which activates and thus cools the thermoelectric cooler stages 8. In contrast, in FIG. 2 (the salt-solution meter) the amplifier 3 controls the power supply 4 which heats the resistive element 8'. The LED regulator 5 is the same for each, as is the optical balance device provided by 6. Readout 7 indicates the "dew temperature" of mirror 9 in the case of FIG. 1 and readout 7' indicates the "salt-solution transition temperature" in the case of FIG. 2 as indicated by a thermometric device 7ak embedded in the mirror just under its reflecting surface. Mirror 9 accumulates the dew from the moist gas passing over the mirror in FIG. 1. In the case of FIG. 2 the mirror 9' is coated with a solution of a deliquescent sensing salt 10 which, at the equilibrium temperature, comprises a mixture of isotropic, saturated salt solution and anisotropic, birefringent salt crystals. In FIG. 2, so as to amplify the signal obtainable from the birefringent crystals, "circular" polarizer 11 first circularly polarizes the light beam from the LED and then analyzes it, as will be explained later.

So as to better understand the essential, primary relationship between the "dew temperature" generated by the hygrometer of FIG. 1 and the "salt-solution transition temperature" generated by the meter of FIG. 2, a review of the characteristics of water-soluble salts such as are used in the hot mirror hygrometry is helpful. The same concepts apply to solid/solid phase transitions as apply to solid/liquid phase transitions.

The function of the sensors is based on the primary phenomenon of hydration. It has been known that some metal salts, MA (which are the stable reaction products of a metal and an acid), react reversibly with water in a stepwise fashion to form hydrates and then a solution. This occurs as the water vapor pressure over the salt varies.

I have discovered that there are some salts whose optical properties in one solid phase are quite different from those in its hydrated (or more hydrated) solid phase. In particular, one solid phase can consist of "optically inactive," cubic crystals whereas the other solid phase can consist of "optically active," non-cubic crystals. In such an instance, at the moment of phase shift (No. 1 below), an optical change occurs which can be readily observed, especially through the use of polarizer "amplifiers." Further, I have found that if the water vapor pressure rises still more, solid, "optically active," non-cubic crystals dissolve to form a solution which is optically inactive (No. 2 below). These phase shifts typify those of a salt sensor useful for solid/solid phase shift sensing:

|  | (1) |  | (2) |  |
| --- | --- | --- | --- | --- |
| MA | ⇌ | MA.sH$_2$O | ⇌ | MA.xH$_2$O |
| Isotropic Solid |  | Anisotropic Solid |  | Isotropic Solution |
| Anhydrous: |  | Hydrated: |  | Dissolved: |
| Cubic Crystals |  | Non-Cubic Crystals |  | No Crystals |
| Non-birefringent |  | Birefringent |  | Non-birefringent |

Figure 3:
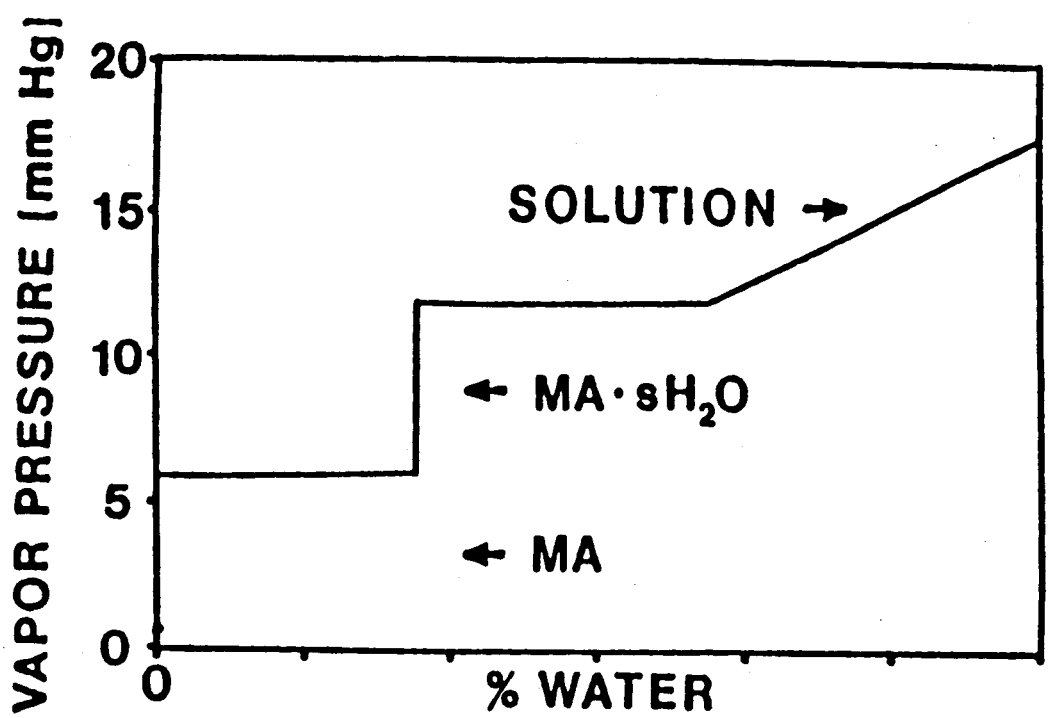
FIG. 3 is a vapor pressure curve for hydrates of a typical salt, MA (where M is a metal cation and $A_t$ is an acid radical), at 20° C.

What is required for solid/liquid phase shift humidity sensing is a birefringent salt which meets the multiple requirement tabulated in the section, "Background of the Invention." Such sensing is shown in phase shift No. 2 above. These mechanisms can be described simply with reference to FIG. 3. If we increase the vapor pressure of water in the presence of anhydrous MA, no reaction occurs until a critical point is reached. Then a hydrate, MA·sH$_2$O, with s representing a specific molecular ratio, starts to form. Any attempt to increase the water vapor pressure is now countered by the formation of more hydrate until all MA has reacted. Only then can the water vapor pressure increase. Because of the relatively easy removal or addition of water, the hydrate water is specifically indicated as H$_2$O, though it is chemically bound.

If the water vapor pressure increases still more, the hydrate deliquesces. That is, the solid removes water from the surrounding atmosphere to form a solution. All soluble solids are deliquescent when the partial pressure of the water vapor in the astmosphere exceeds the vapor pressure of their saturated solution. This technology uses this phase transition point for signalling because it occurs at a very precise and reproducible humidity. As long as any solid remains, any attempt to increase the water vapor pressure results in the formation of more saturated solution. Thus, a very thin, low mass film of signalling salt in equilibrium with a thin layer of saturates solution has the capability of performing as a very responsive sensor. In some instances the solution formed from the deliquescence of a sensor material is undesirable because of its tendency to flow. For this reason, modes of gelling sensor salts have been devised which allow them to signal by passing from solid, opalescent, anisotropic films to clear, isotropic gels at the signalling point.

Figure 4:
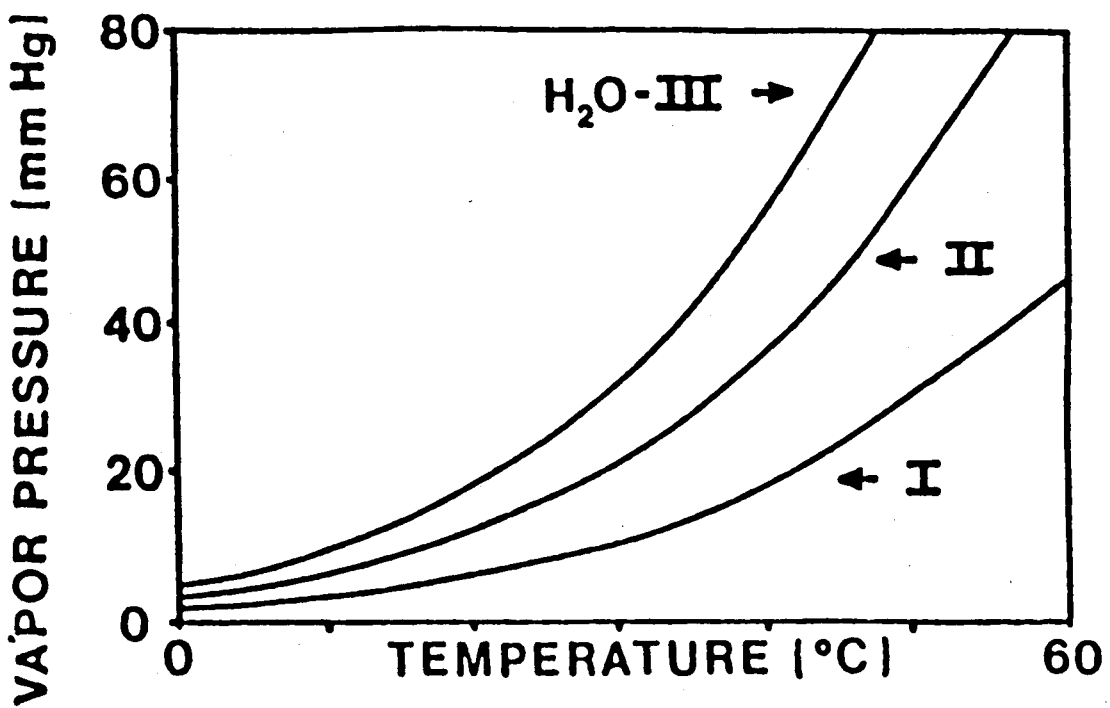
FIG. 4 shows typical vapor pressure-temperature curves for water and hydrates of a salt, MA.

FIG. 4 shows the effect of temperature on the equilibrium of the system described above. On each line the phases stable in the adjacent regions are in equilibrium. The stable solid or liquid phases are: below I, anhydrous; I-II, Ma·sH$_2$O; II-III, solution.

FIG. 5 shows the vapor pressure-temperature curves of water and of a thin film of saturated MA solution, maintained saturated by the presence of a solid phase. The condition at point A is selected for purposes of illustration. If the vapor pressure were decreased to point B by passing the drier gas over the film, water would evaporate and the dry phase would remain. On the other hand, if the vapor pressure were increased to point C by passing a more humid gas over the film, moisture would condense into the solution, the solid salt would dissolve and a solution would remain. The solid/liquid film may be retained at equilibrium when the water vapor pressure over the film changes if the system is heated or cooled to the temperature which places the new vapor pressure on the equilibrium curve of FIG. 5 (points D and E). The temperature at which equilibrium is reestablished indicates the vapor pressure at the new condition. This procedure is the basis for "salt-solution transition temperature" hygrometry. It is exactly analogous to cold mirror hygrometry in which the temperature corresponding to a pre-established water film condition is used as a basis for determination of the vapor pressure. In one case, the vapor pressure-temperature relationship of pure water is used for calculations. In the other, the vapor pressure-temperature equilibrium curve of a particular saturated salt is used. The "salt-solution transition temperature" can be readily converted to the standard "dew point" temperature, of course, by proceeding on a constant vapor pressure line on FIG. 5 until the curve for pure water is intersected. The next section addresses the problem of sensitively detecting the phase shift points of suitable salts.

This technology uses sensing compounds which undergo isotropic/anistropic changes at the phase shift point or "trigger" point. In the isotropic form the optical properties of the cubic crystals and the solution are the same in every direction. The phase shift forms anisotropic, non-cubic crystals which have optical properties which vary with direction. In particular, the crystals have at least two indices of refraction and so are birefringent. Further, the shift from the clarity of the cubic crystal or liquid phases to the opalescence of the non-cubic crystal phase may be amplified readily with polarizers.

Amplification may use the phenomenon of the light blocking which occurs when linear polarizers are crossed or "closed." FIG. 6 illustrates this technique which is used for transmission-type devices. If a solid/solid type humidity sensor in its untriggered, isotropic, cubic crystal phase is placed between the crossed polarizers, the light beam is unaffected and the field is dark. At the moment the trigger humidity is reached, water vapor reacts and the cubic crystals shift to non-cubic crystals which have more than one index of refraction. Such crystals divide a light beam 1 into two rays 2 and 3 as shown in FIG. 7. The second polarizer then resolves the two rays (one retarded and out of phase optically with the other) into one plane-polarized beam which now passed on through. Thus, the "light gate" opens and the sensor suddenly appears to glow brilliantly.

If the humidity continues to rise, the solution phase point of the non-cubic crystals is reached and they begin to dissolve. The optically-responsive, solid phase changes to an optically-inactive, isotropic solution or gel and the light gate closes again. If the humidity drops, the process reverses.

Figure 8:
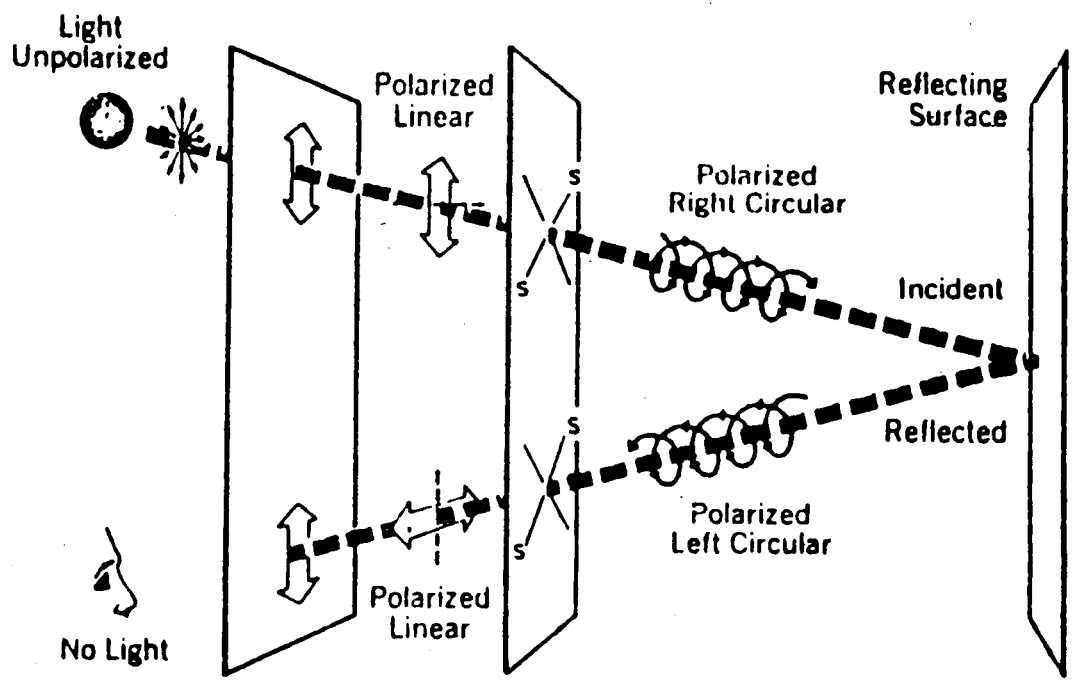
FIG. 8 shows the light transmission in a "circular" polarizer/mirror system.

Reflection-type systems using so-called "circular" polarizers can be readily built. FIG. 8 illustrates the movement of a light beam in a circular polarizer/light reflector system just as FIG. 6 illustrated the movement in a linear polarizer system. The circular polarizer (which comprises a linear polarizer and a quarter wave retarder) produces a circularly polarized light ray having a screw-like movement.

When a circularly polarized light ray is reflected from a mirror, the sense of rotation reverses with the reflection of the ray. The change in both direction and sense of rotation of the light ray results in optical phase changes which bring absorption of the reflected ray by the circular polarizer. Interposing isotropic, cubic crystals or a salt solution between the circular polarizer and mirror leaves the circularly polarized ray unaffected and the field dark. However, at the moment at which the trigger humidity is reached and non-cubic, anisotropic crystals appear, the polarization form of the reflected light is altered and the returning light then passes through the polarizer.

Figure 9:
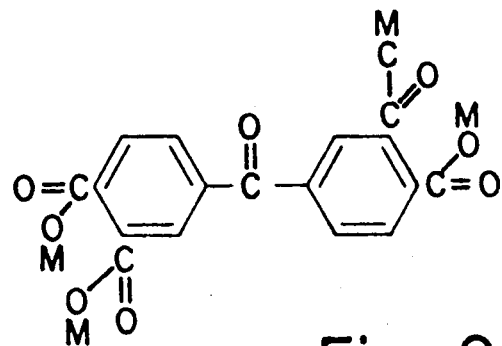
FIG. 9 shows the molecular structure of the metal salt of 3,3',4,4' benzophenone tetracarboxylic acid, a sensing compound most useful in solid/solid phase transition humidity meters of the type described here.

As explained earlier, this technology makes possible hygrometers which function through monitoring concurrent optical shifts as the adjustment of the temperature of sensors exposed to the gas of unknown humidity brings either solid/solid or solid/liquid phase shifts. For solid/solid phase shift sensors the sensing molecule should be highly symmetrical so that the two phases of cubic and non-cubic crystals can shift back and forth for an infinite number of times. FIG. 9 shows the structure of a typical molecule useful for such sensing, namely, the alkali salts of 3,3',4,4' benzophenone tetracarboxylic acids. M in this case is a cation of such alkali metals as Cs, Rb, K, and Na.

Figure 10:
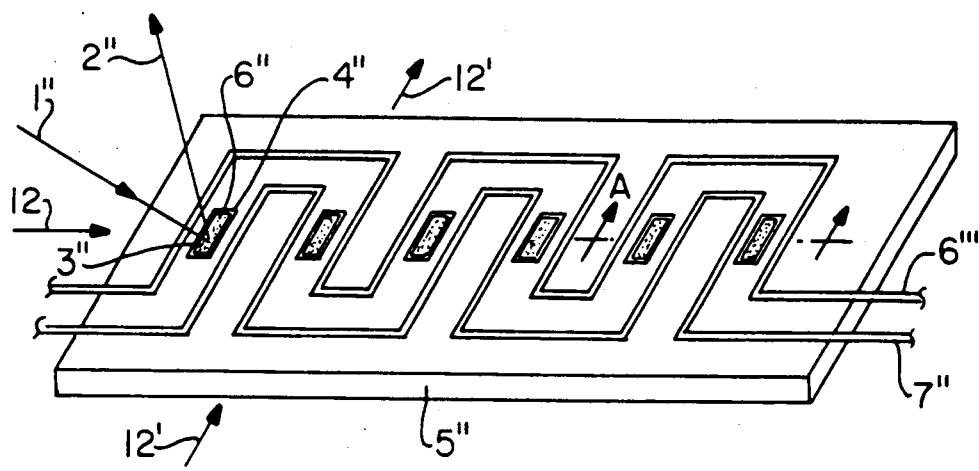
FIG. 10 is a view of a reflection mode hygrometer sensor substrate bearing interdigitated heating and temperature-sending grids with multiple humidity-sensing plaques.

As noted earlier, various types of thermometric sensors can be used for determining the temperature of the sensing salt phases at the equilibrium point. In FIG. 1 and FIG. 2, for example, the thermometric device is inserted within the cooled or warmed metal mirror block and so a thermistor, a thermocouple, or even a stem liquid or bimetallic thermometer could be used. FIG. 10 is a view of a sensing block or stage which uses a platinum resistance thermometer (PRT) 6''' of a grid type, a style widely used. This is because the grid needed to secure a suitable length for electrical resistance can be readily formed using a laser to "etch" a platinum coated substrate 5'' of ceramic, quartz, or material such as berylium oxide for high thermal conductivity. Interdigitated with the PRT in FIG. 10 is a companion grid 7'' of platinum which functions as a resistance heater when suitably powered. In between the two systems are islands of platinum 6'' left by the laser during the etching process. These may be surrounded with a barrier of non-wetting plastic 4'' so as to prevent the "crawling" of the sensor salt 3'' coated onto the platinum mirror 6''. A circularly polarized light beam 1'', such as is shown in the reflection mode system of FIG. 2, reflects off the mirror as beam 2''. The gas 12 whose humidity is to be determined may be passed the length of the stage, as shown. If the gas stream is "dirty," suitable ducts may be provided so as to pass the gas stream 12' across one sensor at a time. When a sensor has been contaminated, the stage is slid sideways so as to position a new sensor so that the light beam 1 reflects from it. Thus, a single PRT/heater/sensor unit can be used for an extended period under dirty conditions without having to clean the stage and recoat with fresh salt solution.

Figure 11:
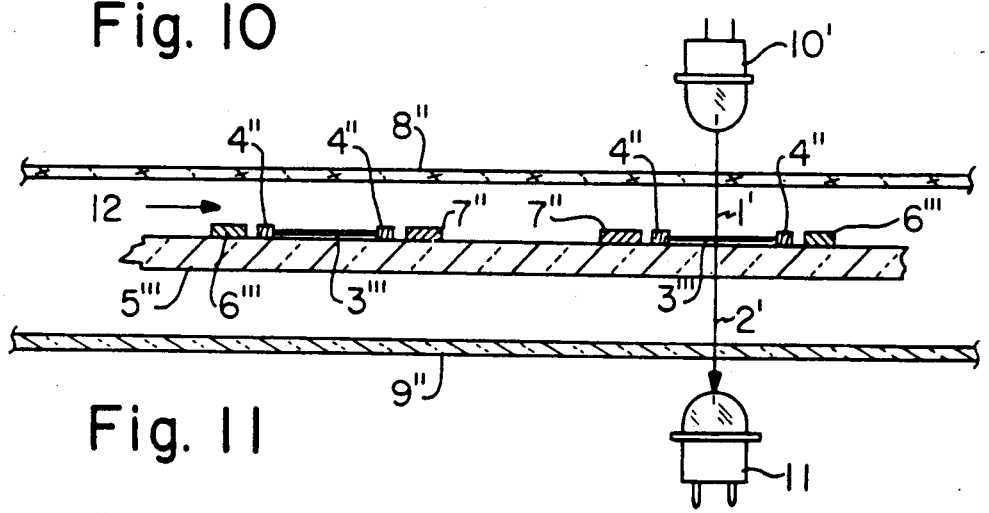
FIG. 11 is a cross-section of a transmission mode system utilizing interdigitated heating and temperature-sensing grids with multiple humidity-sensing plaques.

FIG. 11 is the section A—A' of the substrate of FIG. 10. However, the substrate 5''' is transparent and isotropic since the system is a transmission mode type. That is, the light beam from the LED 10' passes through linear polarizer 8'' to generate polarized beam 1'. This traverses the sensing salt 3''' retained in the "cup" formed by Teflon barriers 4'', 4''. The temperature of the salt and substrate is sensed by the PRT "wire" 6'''. The emerging light beam 2' passes to analyzer 9'' where it may or may not pass depending on whether birefringent crystals have formed in solution 3'''. If the beam passes it activates photodiode 11'. As before, the gas 12 of unknown humidity may be passed the length or width of such a system.

Figure 12:
FIG. 12 is a cross-section of a domed humidity-sensing plaque for use in a system such as is shown in FIG. 11.

FIGS. 12 is a "cup" such as has been used in FIG. 10 and FIG. 11 except, instead of being flat within the Teflon edges 4'' which define the cup, the surface of the substrate 5''' is domed or conically shaped. Under such circumstances the fluid and crystalline salt crystals 3''' are very thin in the center and much thicker toward the edges. The light beam is most desirably passed through the middle where the film is thin. Thus, if a gust of higher humidity gas passes over the sensor area the thin layer of crystals rapidly dissolves and changes the signal output from the photodiode greatly. However, even under severe conditions when all of the center crystals might have momentarily dissolved, the thick layer of crystals at the circumference remains to bring rapid nucleation to the solution in the center as equilibrium conditions are restored. So that the salt solution may wet the Teflon's interior edges, the interior of the Teflon barrier may be dehalogenated with sodium or some similar material. If desired, the Teflon barrier may have undercut inner edges so as to keep crystalline nuclei available even under very difficult conditions.

"Nucleating agents," preferably of isotropic nature, may also be used to prevent or minimize errors in sensing due to all of the salt's own crystals dissolving because of a very rapid rise in ambient humidity. Crystals of the sensing salts rapidly and easily form at and propagate from active sites on the nucleating agent, thus preventing super-saturation and "over-shooting" of the controls. Nucleating agents containing micropores of an appropriate size to hold and maintain the sensing salt in its crystalline form (from which pore apertures the saturated solution can be nucleated) are also useful.

Besides nucleating agents (or as a combination agent in some instances) catalysts can be compounded with the humidity-sensing chemical composition to lower the activation energy so that hydration and dehydration occur more readily. Materials which are isotropic or of a low degree of anisotropy are required so as to not interfere with optical signalling. Finely divided particles having a high intrinsic surface area with catalytic sites are required. Zeolites, alkali/magnesium silicates, and many precipitated or fumed aluminum, titanium, and silicon oxides are very active. As is well known, the precise mode of processing catalysts and the presence of trade "impurities" can substantially modify catalytic activity. However, catalysts can be readily evaluated for efficiency by noting the reduction of undershoot and/or overshoot in a system using a humidity-sensing salt compounded with the candidate catalyst.

Generally, concentrations of from 0.1 to 5.0% by weight of the nucleating agent (on the basis of the weight of contained sensing salt) have proven to both nucleate and thicken the sensing salt to prevent undesirable flow.

Figure 13:
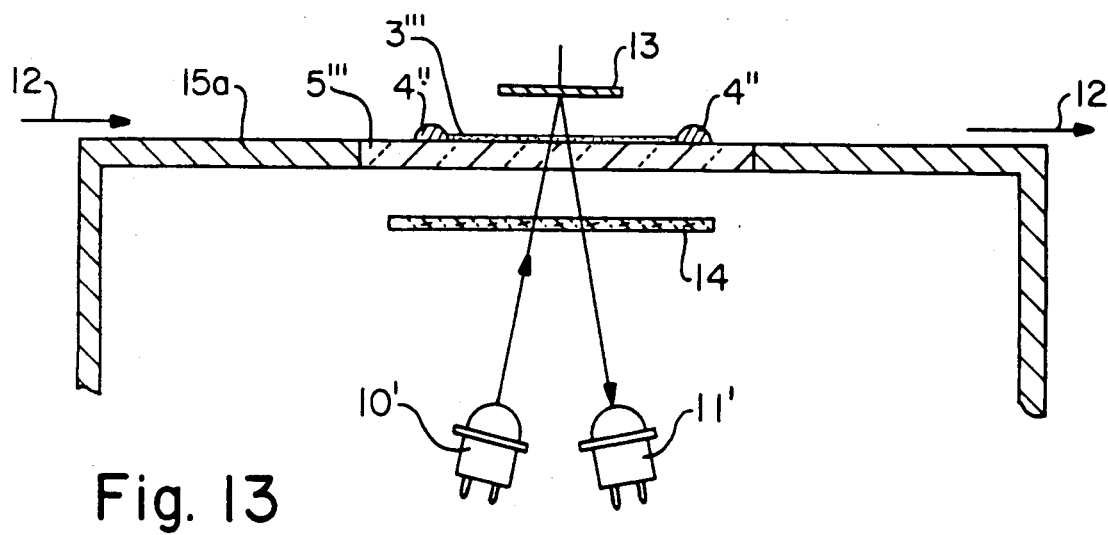
FIG. 13 is a cross-section of a reflection mode system suitable for easy cleaning.

FIG. 13 is a reflection mode system not unlike that of FIG. 2. However, to produce a very streamlined housing which is easy to clean, the LED 10' and the photodiode 11' are below the housing 15a. The light beam passes through the circular polarizer 14, through the transparent substrate 5''', through the salt 3''', to the reflector 13. There it is reflected back toward photodiode 11, either passing through circular polarizer 14 or not, depending on whether or not birefringent crystals are present. The gas stream 12 can be passed across the stage in various directions and, though not shown, the substrate and salt film are suitably heated and their temperature sensed as before. Instead of an overhead reflector 13, which is the only thing preventing very "clean" lines, a few metal flakes of high reflectance and resistant to corrosion by the metal salt used can be distributed on the salt crystal/solution surface to serve as an in situ reflector. A very thin metal reflector perforated with myriad holes to give a high degree of openness also can be floated on the surface of the salt crystal/ solution to serve as a reflector.

FIGS. 14, A and B, show cross-sections of another type of reflection mode system which also has a very cleanable stage. The light beam 1''' is projected into heated and temperature-sensed isotropic, clear prism 5b. When the sensing salt is in isotropic solution form 3' FIG. 14B the light beam undergoes total internal reflection and emerges as beam 2''' (FIG. 14B). This is because the refractive index of the solution is less than that of the glass prism. When the heated solution forms polycrystalline, anisotropic crystals 3'' of higher refractive index than the prism, much of the beam 1''' escapes through the upper surface and emerging signal 2''' is much attenuated as it is directed to a suitable detector (FIG. 14A).

The light beams are shown as being "piped" to the prism sides using optic fibers, but other arrangements can be used. In some cases, the prism can be dispensed with and optic fibers used to bring a light beam to and from the under side of a clear, isotropic, heated and temperature-monitored, flat plate carrying the sensing salt. Just as with the prism, the detector responds to the shift in the amount of light reflected at the salt/substrate interface as the solution/crystal ratio varies.

A useful modification of the grid system of FIG. 10 is to place the platinum resistance thermometer (PRT) 6''' on one side of the substrate 5'' and the resistance "wire" grid 7'' on the opposite side. In such a case the resistance element may be of a different material. Further, its mechanical configuration may be designed so as to secure preferred thermal gradients or to leave apertures for light beams in transmission mode systems, etc.

If the beam being reflected from the interface of an isotropic substrate/salt film has its angle of incidence and reflection empirically adjusted, the signal shift obtained when the solution/crystal ratio varies can be readily maximized. FIG. 14 does not show the use of linear or circular polarizers, and sometimes it is not necessary, though often the use of polarizers produces enhancement of the signal shift as the solution/crystal ratio varies. The same situation obtains with regard to a light beam piped to and from a flat plate covered with a sensing salt using fiber optics.

Using a linear polarizer as an analyzer, the change in Brewster's angle (as the solution/salt ratio of a heated sensing salt film shifts) can also be used to modulate the intensity of a light beam reflected from the upper, gas-sensing surface of the film.

Still another useful variant of a configuration such as FIG. 10 (or its double-sided modification just described) is to coat the heating and/or temperature-sensing elements with thin coatings of salt-and thermally-resistant coatings. There are various polyimides, "Parylene" films, silicones, and other polymeric insulating films which may be used to coat the elements. In such instances, the sensing salt solution/crystals can be deposited without the care needed to prevent electrical "shorts" such as is practiced in FIG. 10. Barriers to prevent salt crawling can be formed on the insulating film. As before, non-oxygen bearing polymers of the fluorinated type, sometimes characterized as "Teflons," perform well. The latter includes polychlorotrifluoroethylene, polytetrafluoroethylene, PFA fluoroplastics, FEP fluoroplastics, polyvinylidene fluoride, and PECTPE.

In addition to the conformal coatings over the heating and/or temperature sensing elements for electrical insulation, a conformal coating of about 0.0001 in. may be applied over the salt film once it is deposited in its "cup" or in some appropriate area. The salt film may be deposited as a solution, dried, and then dipped in a solution of the conformal coating and dried again. In such a case a conformal coating is selected which has both a high moisture transmission rate and good thermal stability. A number of silicones, polyvinyl alcohols, polyvinyl acetates, cellulose acetates, and other polymers possess these characteristics. Thus, in use, contaminating dust, salts, and other debris can be wiped off of the conformal coating without disturbing the sale crystals/salt solution sealed under. Though such a system is not as rapidly responsive as the open salt film, it has many useful applications in industry where speed of response is not critical.

In systems where a very "dirty" atmosphere is being gauged, the humidity-sensing salt solution may be intermittently or continuously flowed across the mirror so that a fresh sensing film is frequently or continuously exposed to gas whose humidity is being measured. If desired, the mirror may be vertical so that there is a gravity flow of solution to cleanse the mirror. An equilibrium mode of operation (both salt and solution present concurrently) gives the greatest accuracy. Thus, it is usually desirable to use a heated mirror of such size that, before the sensing salt crystals and solution pass across the optically scanned section of the mirror, the solution has had an opportunity to come into equilibrium with the gas being sensed.

Thermistors are available in various configurations such as beads, flakes, and cylinders. Some are very small and so are rapidly responsive. They may be heated by passing current through them or they may be used in the sensing mode. In the latter case, the thermistor's ambient temperature may be determined from its resistance. Thus, if two thermistors are mechanically bonded in such a way as to secure a low thermal resistance, they may comprise a suitable stage or mount for a sensor salt film. One of the thermistors may be coated with an inert reflecting surface such as gold, platinum, or stainless steel to carry the sensing salt. As before, Teflon or similar non-wetting barrier films or edges may be provided to constrain the salt solution/crystals.

Since the thermistor element is often sealed within a clear glass structure for mechanical protection, the thermistor can be readily operated in the transmission mode. The glass thermistor "housing" can serve as the stage or mount for the salt sensing film just as substrate 5''' in FIG. 11 carries the sensing salt 3'''.

Systems may be operated in which a single thermistor is used as both a heater and a temperature sensor. Commutation, either mechanical or electrical, is used to connect the thermistor for a short interval to a heating power circuit and then to connect it to a resistance measuring circuit to measure temperature. Heating and measuring is continued alternately to reach and maintain the sensing salt/solution at the equilibrium point.

Instead of using very fine round wires as some platinum resistance thermometers do, thin, wide flat wires may be wound in a spaced, helical configuration on a heated, Teflon coated cylinder, a segment of each wire turn being polished to a mirror finish to carry a small deposit of sensing salt. The spread of the salt solution can be controlled as before using Teflon barriers. Thus, a helix of even moderate length can carry a number of side-by-side mirror segments, all facing in a common direction, which can be moved sequentially under the LED/photodiode optical system for scanning as any particular segment is contaminated by dirty gases.

Instead of using true wide, flat wires as described above, the width of the flat grid film of platinum shown in FIG. 10 can be increased so that the platinum, temperature-sensing film comprising the PRT also serves as the mirror mount for the salt film. Thus, whereas in FIG. 10 the salt film 3''' is between PRT 6''' and heater 7'' (surrounded by non-wetting barrier 4), in the modified version film 3'''would be on the platinum film (made wider) of PRT 6'''.

The optoelectronic emitter/detector can be greatly varied, as noted before. Combination emittor/detectors are available at low cost which create a light spot as small as 0.17 mm. Thus, hygrometric systems using such small, scanned spots can be very compact. There are other advantages to such small systems. If the area of the salt sensing film is very small, it is held in its sensing position by surface tension alone, independent of its position. Thus, the sensing salt need not be "thickened" with finely divided solids or chemical complexes as it must be to prevent drainage problems when large area sensing films are used.

As would be expected, the accuracy of the sensing can often be increased by designing the system so that the gas whose humidity is being sensed is in complete equilibrium with the salt sensing film. Thus, the gas can be directed across the sensing film using fins and ducts so as to produce turbulence and to minimize the thickness of the stagnant boundary layer above the sensing film. Where the heated stage is relatively long, as with PRTs, the gas can be directed to traverse the length of the heater/sensing element (in a helical manner, if desired) so that the temperature of the gas/salt film/PRT is known with great exactness. Judicious insulation of the sensing elements can also assist in securing true equilibrium conditions.

As noted in the description of the sensing elements, very thin films are desired for signalling so as to secure sensitivity. They may be much thicker at the edges as shown. In general, the scanned area is preferably from about 0.0001 in. to 0.0005 in. though much thicker films can be used where speed of response is not a factor and where great resistance to contamination from "dirt" is desired.

The polarizers used with these various hygrometers can be of "standard" linear or of circular type or they can be of the heat-resistant type if the polarizers in a particular device are close to the heated sensing film. Though visible light is preferred for these systems, infrared can be used so long as infrared polarizers are used. So-called "chopped beams" are preferred as the source of illumination so as to make the systems immune to error from ambient un-chopped light which may leak into the system.

If the temperature of the salt/solution at equilibrium is known, the dew temperature can be readily obtained from the empirical curve discussed before. If the relative humidity, rather than the absolute humidity is desired, the ambient temperature of the gas stream being sampled is determined as well. From the vapor pressure of water at the ambient temperature and at the dew temperature the relative humidity can be readily calculated. This can be done automatically using suitable IC chips as part of the instrument if desired.

The thermometric device used for determining the ambient temperature can be the same as or different from that used to determine the salt-solution temperature. It is only important that it has suitable accuracy and can readily sense the temperature of gas streams rapidly.

Obviously, the electrical signal from the thermometric device can be used for electrical control means in place of or as an adjunct to a "salt-solution transition temperature," or "dew temperature," or a "relative humidity" readout. Such a signal can be amplified as desired for control purposes. Various standard methods may be used to process the signal(s) generated by the thermometric device(s) so as to convert them into appropriate readouts.

Suitable standard methods can be used for amplifying the electrical signal from the optical detector and for using the electric control signal thus obtained to adjust the temperature of the salt-solution heater to bring it to the equilibrium temperature of the two phases and maintain it there.

As noted before, modulated systems are preferred for maximum accuracy. However, the myriad applications, "on-off" systems function nicely. For example, present residential and commercial humidistats based on nylon sensing webs are very inexact and drift seriously with aging. Thus, a great need exists for accurate, non-drifting humidistats which are at least as accurate and response as the nylon web type. Through using simple "go-no go," "dark field-bright field" sensing and control, inexpensive humidistats can be made which meet these requirements. Thus, there is a place for both the high precision, equilibrium type of operation and the lower accuracy, stable, non-drifting control which functions on an on-off basis. In the latter case, of course, the control point oscillates between salt solution with no crystals and solution with crystals.

FIG. 15 is a view of one simple type of humidity control which performs in this way. It is one in which the bimetallic arm 4''' of an electromechanical "thermostat" (controlling a dehumidifier) is located spatially close to the salt film's mirror 5' and heater 6' so that there is thermal coupling between them. The photo detector 2, located so as to receive light passing through polarizer 13' from the salt film 3'' is a photoresistor type operating as a shunt across the combination salt film/"thermostat" heater powered by lines 11'' and 12''. As the film of salt solution is heated and dried sufficiently to generate birefringent, non-cubic crystals, the resistance of the photoresistor drops and it shunts power away from the heater of the salt film/"thermostat." Thus, the heater cools, the "thermostat" contacts open, opening power circuit 9''' and 10''', so the dehumidifier 8'' turns off. The cooling, birefringent salt film crystals then dissolve so that the photoresistor no longer shunts power away from the heater, and so the cycle continues. The same basic arrangement can also control a humidifier.

We have now considered the way in which the signalling salts function and representative apparatus in which they may be used. The special salts which I have now found to meet the needs of "hot mirror" hygrometry can now be better understood as part of a complex whole.

Earlier I noted that long term stability at elevated temperatures, a low tendency to supersaturate, a high degree of birefringence, a high melting point, a rapid and reversible response to shifting equilibrium points, and very high water solubility were among the desired characteristics of suitable sensing salts.

High thermal stability is needed over extended periods. Any degradation would form new compounds whose salt-solution water vapor pressure-temperature equilibrium curves would be entirely different from those of the "parent" compound. This would seriously affect the accuracy of the instrument.

In the earlier patents, referred to before, excellent accuracy was obtained by monitoring the optical readout as one phase changed to another. For the purpose of securing still greater accuracy as well as a continuous readout, this technology is especially concerned with an equilibrium mixture of two phases. That is, for accuracy a mixture of a chemical composition's non-cubic and cubic crystals is monitored optically in the case of a solid/solid phase, hot mirror hygrometer. Likewise, a mixture of a composition's non-cubic crystals and its saturated solution is monitored in the case of a solid/liquid phase, hot mirror hygrometer.

In the earlier patents I claimed compounds whose saturated solution at 20° C. had a vapor pressure of from 17.5 to 1.0 mm of mercury. The range of the new series extends from 17.5 to 0.1 mm of mercury in order to encompass sensors of very high water solubility which allow sensing in the industrially important low humidity ranges as well as in the very high humidity ranges so important in the electronics field.

Regarding compounds which have met the new, rigorous needs imposed by hot mirror hygrometry, I have found that the alkali metal salts of aliphatic acids, of hydroxy aliphatic, of keto aliphatic, and of ketohydroxy aliphatic acids which have six carbon atoms or less are especially useful for my requirements. The alkali metal salts of aliphatic sulfonic acids of six carbons or less are also very useful. Further, I have also found that the alkali metal salts of these acids, in which at least one hydrogen has been replaced with fluorine are of exceptional value as sensors because of their enhanced heat stability.

The pure alkali salts of these acids may be used. However, I have found that mixtures of salts of different alkali metals, such as potassium and rubidium or rubidium and cesium, of the same aliphatic acid often confer improved properties such as greater solubility and superior signalling characteristics. They form "solid solutions" or "mixed crystals" in which homogeneous crystals form having properties intermediate between those of the pure salts used.

The vapor pressure of the saturated solution of these mixed crystal compositions also is intermediate between the pressure exhibited by the saturated solutions of the pure salts. This property can be most useful in preparing humidity sensing compositions which undergo phase shifts and thus signal at precise, preestablished vapor pressures. Besides solid solutions containing mixed cations, the aliphatic anions also often can be mixed in the same way to create superior signalling compositions.

Of the alkali salts, I have found that the cesium and rubidium salts are often of great utility because of high water solubility. However, understanding of the complex interaction between the anion and the cation of salts and water is very limited, and so no reasonably accurate mode of theoretically predicting water solubility is known. Thus, an extensive synthesis of salts and evaluation of their properties under the complex conditions of hot mirror hygrometry has been essential. Examples of salts which possess the combination of unusual properties required include cesium formate and acetate among the aliphatic acids, the sodium, potassium, rubidium, and cesium salts of glycolic acid among the hydroxy aliphatic acids, the rubidium and cesium salts of levulinic acid among the keto aliphatic acids, the cesium salt of trifluoroacetic acid among the fluorinated aliphatic acids, and the rubidium salts of methane sulfonic acid among the aliphatic sulfonic acids.

My focus has been on sensors which are suitable for hot mirror hygrometry. However, I have found that such sensors also are quite suitable for a variation of hot mirror hygrometry. In particular, for many applications, for example the controlling of relative humidity (RH) in the 52-55% range around computers during the winter time (so as to prevent damage from static electricity), it is clearly not necessary to be able to select a wide range of humidities. Where only one basic RH set point is necessary, holding a particular sensing salt at one particular, preset temperature will cause it to function nicely as the controlling optical sensor. Scanning the constant temperature salt film optically in order to monitor its state of birefringence (solid) or non-birefringence (liquid) generate an on/off signal which may be suitably used for controlling humidity-modifying equipment.

Controlling over a single, narrow range (such as 52–55% RH) may be further simplified by selecting an optically responsive salt which begins deliquescence at the desired relative humidity at a particular room temperature. It is then necessary to heat the sensing salt since it is already operating at its appropriate temperature. Further, salts may be empirically selected whose vapor pressure-temperature equilibrium curves change proportionately with that of water (or close to it). Thus, though the vapor pressure of the solid/liquid equilibrium curve for the salt varies with temperature, the relative humidity stays almost constant. This is because RH=100×vapor pressure of salt/solution÷vapor pressure of water.

As an illustration of this latter type of salt, magnesium nitrate deliquesces (that is, the birefringent salt and its saturated solution are in equilibrium) at approximately 54.9% RH at 20° C., 53.4% RH at 25° C., and 52.2% RH at 30° C. THus, it is an excellent sensor salt for a low cost humidity control for humidifiers for computers. Over the desired temperature range its equilibrium RH falls within the desired 52–55% RH range.

These salts, though they may be operated at room temperature as a matter of convenience, are as much "hot mirror" sensing salts as those which may be operated at a 40° C. higher temperature. Indeed, the same salt might be operated, depending on application, at (1) a variable, elevated temperature, (2) a constant, elevated temperature, or (3) a relatively constant room temperature.

The salts, as noted, can be scanned by the eye or by various optoelectric devices. A series of salts of the type just described can be assembled in which each salt film at room temperature undergoes its solid/liquid phase shift at an incrementally different water vapor pressure. For example, at room temperature one might undergo its solid/liquid phase shift (bright/dark optically when polarizer amplified) at 30% RH, the next at 40% RH, etc. in 10% intervals. A "light gate" can be formed of discrete, adjacent areas on a suitable substrate, each containing a thin layer of a salt of the type just described, each salt shifting phase at a selected RH. When such an assembly, on a transparent, isotropic substrate, is interposed between crossed, linear polarizers, it becomes a humidity-responsive light gate. When placed between a photo emitter and a suitable photo-responsive device a change in humidity generates a stepwise change in light output and thus a similar change in current or voltage from the photo-responsive device.

The same assembly comprises a solid/liquid phase shift hygrometer, of course, if suitable relative humidity scales are placed in juxtaposition with the separate sensor areas. FIG. 16 shows such a hygrometer. Crossed, linear polarizers 11''' and 14'' are illuminated by light source 15. Transparent or translucent, isotropic substrate 2''' is coated with discrete areas 13'',13''',13'''', etc. of sensing salt films which undergo a solid/liquid, humidity-responsive phase shift. Viewer 61 scans the system through analyzer 14''.

The advantage offered by light gates which use solid/liquid phase shift sensors is illustrated in FIG. 17. Solid/solid phase shift sensors pass through three optical shifts as the humidity changes, namely, from dark field, to bright field, and back to dark field. This is shown in FIG. 17A and it makes such sensors difficult to use in controls. On the other hand, solid/liquid (gel) phase shift sensors undergo a simple bright field/dark field change and this makes them easy to use in light gates for use in controls. This sequential, stepwise shift in light output with the change in humidity over the sensors is shown in FIG. 17B.

Humidity-sensing salts which undergo solid/liquid phase shifts may exhibit undesirable fluid flow under the influence of gravity and a high humidity level. Earlier it was noted that certain finely divided solids could nucleate sensing salt solutions as well as thicken them to minimize flow. Frequently, thickening of sensing salt solutions with suitable chemical complexes is more desirable than thickening with powders. Or, sometimes, it is desirable to thicken chemically as well as with powders.

In U.S. Pat. No. 4,166,891 I revealed that the tetraalkali salts of the unusual cyclic compound 3,3'4,4' benzophenone tetracarboxylic acid could be complexed so as to form a concentrated, gelled film of the sensing salt. It was accepted that, because this compound was cyclic and polyfunctional, having four carboxyl groups, a vast, three-dimensional network of cross-linked metal ions, polymers, and carboxylates formed. Such a system meets the rule for forming gels, namely to utilize polyfunctional compounds compatigle with the particular system. Unexpectedly, I now have found that the alkali metal salts of certain simple, aliphatic acids may also be gelled, through some unknown mechanism. These salts are of great value as signalling agents in the present technology. In particular, they are those chemical compositions which undergo a solid/liquid (gel) phase change at suitable water vapor pressures, the phase change being accompanied by a shift from non-cubic, birefringent crystals to isotropic solution.

Such compositions, when they are the alkali salts of suitable acids, can be gelled with from 0.5 to 25.0 mol percent of the metals present a water-soluble salt of a polyvalent metal cation selected from the group $Cu^{++}$, $Mg^{++}$, $Ca^{++}$, $Sr^{++}$, $Ba^{++}$, $Zn^{++}$, $Cd^{++}$, $Al^{+++}$, $Cr^{+++}$, $Mn^{++}$, $Co^{++}$, and $Ni^{++}$, and in which each 15% of the alkali metal salts is complexed with from 2 to 10% by weight of a polymer which has repetitive carboxyl groups whose acidic hydrogens have been replaced by alkali metal cations. For superior heat stability the polymer can be eliminated. For superior gelling or viscosity stabilization an alkali metal borate can be included with the complexing agents described above in an amount from 0.25 to 16.0 mol percent of the metals present.

What is claimed is:

1. An optical-type, humidity-responsive device for monitoring ambient humidity comprising (1) a source of illumination providing a light beam, (2) means for providing observable change in humidity comprising a film of a heat-stable, high birefringent, high melting point solid/liquid composition which of itself can rapidly and reversibly sense changes in the ambient humidity, which composition has a hydrated solid anisotropic and translucent salt phase characteristic of a first condition and a liquid isotropic and clear phase characteristic of a second condition, the solid/liquid composition comprising (1) a saturated aqueous salt solution and (2) a hydrated solid salt portion in said solution, said solid hydrated salt portion being maintained concurrently in equilibrium with the salt solution at any ambient humidity, the solid salt being birefringent and translucent and the solution being non-birefringent and optically clear, the rate of evaporation being equal to the rate of condensation at the surface of the film of the salt solution at its transition temperature, the solid/liquid composition's equilibrium being abruptly triggered at a particular level of water vapor pressure and temperature which is characteristic of and indicates a change in the ambient humidity, the salt being an alkali metal salt of an acid selected from a member of the group consisting of aliphatic, keto aliphatic, aliphatic in which at least one hydrogen is replaced by fluorine, hydroxy aliphatic, hydroxyketo aliphatic, and mixtures thereof, (3) means for determining the transition temperature of the solid/liquid composition at the phase change transition point characteristic of any ambient humidity, (4) means for variably heating said solid/liquid composition film on a substrate to maintain the composition at the transition temperature at which phase change occurs, (5) light detecting means for detecting a visual signal of preselected brightness and intensity resulting from the composition intercepting the beam of light from the source of illumination at the transition temperature, said visual signal changing brightness and intensity in response to the triggering of the composition resulting from a change in the ambient humidity representation of a new ambient humidity and to define a correspondingly different visual signal, (6) means connecting said different visual signal to said heating means to activate the same and to adjustably maintain the composition at the transition temperature characteristic of the new ambient humidity, and (7) means for determining ambient humidity using the transition temperature at said transition point and the known vapor pressure of the salt solution at the transition temperature, and wherein there is a predetermined relationship between the vapor pressure versus temperature equilibrium curve of pure water and that of the saturated salt solution thus defining the particular solvent/liquid composition's equilibrium curve for the phase change sensed in which the saturated aqueous solution of the composition has a vapor pressure in the range of about 0.1 to 17.5 mm of mercury at 20° C., and whereby any equilibrium point of the chemical composition is related to an equivalent dew point of pure water.

2. An optical-type, humidity-responsive device as is defined in claim 1 and wherein the light detecting means is operable to detect the visual signal of preselected brightness and intensity with a predetermined range.

3. A device as defined in claim 1 in which the means for providing observable changes includes means to intensify observable changes comprising a polarizer for polarizing the light beam and an analyzer for analyzing the beam, the light beam traveling through the device by going through the polarizer and the polarized light passing through the composition that doubly refracts the beam when birefringent at the first level of vapor pressure/temperature to pass the beam on through the analyzer.

4. A device as defined in claim 2 in which the means for providing observable changes includes means to intensify observable changes comprising a polarizer for polarizing the light beam and an analyzer for analyzing the beam, the light beam traveling through the device by going through the polarizer and the polarized light passing through the composition that doubly refracts the beam when birefringent at the first vapor pressure/temperature to pass the beam on through the analyzer.

5. A device as defined in claim 1 in which the light detecting means includes electrical means responsive to the visual signal characteristic of said first condition and non-responsive to the signal characteristic of said second condition.

6. A device as defined in claim 5 in which the electrical means includes a photo-responsive solid state electronic device.

7. A device as defined in claim 5 in which there is electrical control means that is responsive to the visual signal, the control means for controlling electrical power to activate an electrical circuit.

8. A device as defined in claim 2 in which the means for heating said composition to the temperature at which the anisotropic/isotropic phase is in equilibrium at the particular water vapor pressure upon the solid/liquid composition includes means for maintaining said anisotropic/isotropic phase at the equilibrium temperature.

9. A device as defined in claim 1 in which the composition comprises the rubidium or cesium salt of an aliphatic acid.

10. A device as defined in claim 1 in which the composition is selected to trigger at a particular water vapor pressure at room temperature.

11. A device as defined in claim 1 in which at least two discrete areas which are adjacent in the same plane are occupied with compositions comprising a series of compounds or mixtures of compounds which trigger at different water vapor pressures at room temperature.

12. A device as defined in claim 1 in which the means for providing observable changes includes means to intensify observable changes comprising a polarizer for polarizing the light beam, the light beam travelling through the polarizer and the polarized light passing through the composition that doubly refracts the beam when birefringent at the first vapor pressure/temperature to a mirror and then being reflected back through the composition and analyzer.

13. A device as defined in claim 11 in which the composition film is a coating of at least about 0.0001 in. and said substrate 15 a transparent or translucent isotropic substrate.

14. A device as defined in claim 13 in which the composition coating is protected by a water vapor permeable, polymeric, isotropic, transparent, conformal coating at least about 0.0001 in.

15. A device as defined in claim 1 in which from 0.1 to 5.0% by weight of a finely divided, substantially isotropic thickening and nucleating agent, on the basis of the contained weight of chemical composition, is included in said composition.

16. A device as defined in claim 11 in which the composition is complexed with (1) the water-soluble salts of polyvalent metal cations selected from the group $Cu^{++}$, $Mg^{++}$, $Ca^{++}$, $Sr^{++}$, $Ba^{++}$, $Zn^{++}$, $Cd^{++}$, $Al^{+++}$, $Cr^{+++}$, $Mn^{++}$, $Co^{++}$, and $Ni^{++}$, (2) the water-soluble salts of a polymer which has repetitive carboxyl groups whose acid hydrogens have been replaced by alkali metal cations, and (3) a water-soluble alkali metal borate.

17. A device as specified in claim 1 in which the salt is cesium formate.

18. A device as specified in claim 1 in which the salt is cesium acetate.

19. A device as specified in claim 1 in which the salt is cesium glycolate.

20. A device as specified in claim 1 in which the salt is rubidium levulinate.

21. A device as defined in claim 1 in which the substrate is hydrophilic, the chemical composition being deposited upon the substrate.

* * * * *